(12) United States Patent
Hegel

(10) Patent No.: US 9,810,651 B2
(45) Date of Patent: Nov. 7, 2017

(54) METHOD AND DEVICE FOR HANDLING A CLOSING ELEMENT IN A LABORATORY AUTOMATION SYSTEM

(71) Applicant: Roche Diagnostics Operations, Inc., Indianapolis, IN (US)

(72) Inventor: Markus Hegel, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 168 days.

(21) Appl. No.: 14/962,223

(22) Filed: Dec. 8, 2015

(65) Prior Publication Data

US 2016/0178550 A1 Jun. 23, 2016

(30) Foreign Application Priority Data

Dec. 18, 2014 (EP) .................................... 14199002

(51) Int. Cl.
| | | |
|---|---|---|
| *G01N 27/04* | (2006.01) | |
| *G01N 35/00* | (2006.01) | |
| *B01L 3/00* | (2006.01) | |
| *G01N 35/04* | (2006.01) | |
| *B65B 7/28* | (2006.01) | |

(52) U.S. Cl.
CPC ........ *G01N 27/041* (2013.01); *B01L 3/50825* (2013.01); *G01N 35/00* (2013.01); *G01N 35/04* (2013.01); *B01L 2300/046* (2013.01); *B65B 7/2807* (2013.01); *G01N 2035/0403* (2013.01)

(58) Field of Classification Search
CPC ...... G01N 17/00; G01N 17/006; G01N 17/02; G01N 27/00; G01N 27/02; G01N 27/04; G01N 27/041; G01N 35/00; G01N 2035/0403; G01R 27/00; G01R 27/02; G01R 27/04; G01R 27/26; B01L 3/50; B01L 3/508; B01L 3/5082; B01L 3/50825; B01L 2300/04; B01L 2300/046; B65B 7/00; B65B 7/16; B65B 7/28; B65B 7/2807
USPC .......................... 324/600, 649, 691, 693, 722
See application file for complete search history.

(56) References Cited

U.S. PATENT DOCUMENTS

| | | | |
|---|---|---|---|
| 4,750,312 A | 6/1988 | de Vaujany | |
| 4,816,110 A | 3/1989 | Foldesi et al. | |
| 6,585,163 B1 * | 7/2003 | Meunier | .......... G06K 19/06028 |
| | | | 235/385 |
| 9,568,414 B2 | 2/2017 | Menges et al. | |

(Continued)

FOREIGN PATENT DOCUMENTS

| | | |
|---|---|---|
| CN | 102435614 A | 5/2012 |
| EP | 0405017 A1 | 1/1991 |

(Continued)

*Primary Examiner* — Hoai-An D Nguyen
(74) *Attorney, Agent, or Firm* — Roche Diagnostics Operations, Inc.

(57) ABSTRACT

A method and a device for handling a closing element in a laboratory automation system are presented. The closing element is a sealing foil having at least two layers forming a first surface and an opposing second surface, respectively. The layers differ in at least one material property. The material property on at least one of the first surface and the second surface for identifying the orientation of the sealing foil is determined. A laboratory automation system for carrying out the method and/or with the device is also presented.

20 Claims, 2 Drawing Sheets

(56) References Cited

U.S. PATENT DOCUMENTS

| | | | |
|---|---|---|---|
| 2003/0016980 A1* | 1/2003 | Meunier | G06K 19/06028 400/76 |
| 2003/0041656 A1* | 3/2003 | Neo | G01B 11/303 73/105 |
| 2004/0043608 A1* | 3/2004 | Katagiri | B23H 5/08 438/672 |
| 2006/0018969 A1* | 1/2006 | Figueroa | A61K 9/0053 424/489 |
| 2012/0087848 A1 | 4/2012 | Nakahana et al. | |
| 2012/0244541 A1 | 9/2012 | Rapp | |
| 2013/0100503 A1* | 4/2013 | Beselt | H04N 1/128 358/474 |
| 2014/0354968 A1* | 12/2014 | Suda | G02B 7/28 355/55 |
| 2015/0276639 A1* | 10/2015 | Spath | G01N 27/041 324/697 |
| 2016/0237549 A1* | 8/2016 | Hara | C23C 14/205 |

FOREIGN PATENT DOCUMENTS

| | | | |
|---|---|---|---|
| EP | 2431747 A1 | 3/2012 | |
| JP | 2005-162306 A | 6/2005 | |
| JP | 2009-168761 A | 7/2009 | |

* cited by examiner

METHOD AND DEVICE FOR HANDLING A CLOSING ELEMENT IN A LABORATORY AUTOMATION SYSTEM

CROSS-REFERENCE TO RELATED APPLICATIONS

This application claims priority to EP 14199002.8, filed Dec. 18, 2014, which is hereby incorporated by reference.

BACKGROUND

The present disclosure generally relates to laboratory automation systems and, in particular, to a method and a device for handling a closing element in a laboratory automation system.

Typically, a laboratory automation system comprises a number of pre-analytical, analytical and/or post-analytical stations, in which samples, for example blood, saliva, swab and other specimens taken from the human body, are processed. It is generally known to provide test tubes containing the samples. Prior to processing, the test tubes are usually capped with a removable plug or stopper. For processing the samples, the test tubes are decapped. After or during processing, the decapped test tubes are reclosed in order to prevent contamination of the sample and/or to store the sample inside the test tube. In order to reclose the test tubes, a closing element is provided. A correct handling of the closing element is necessary to allow for a proper closing of the test tube.

Therefore, there is a need for a method and a device for an improved handling of a closing element in a laboratory automation system.

SUMMARY

According to the present disclosure, a method and device for handling a closing element in a laboratory automation system is presented. The closing element is a sealing foil having at least two layers forming a first surface and an opposing second surface, respectively, in which the at least two layers differ in at least one material property. The material property on at least one of the first surface and the second surface is determined for identifying the orientation of the sealing foil.

Accordingly, it is a feature of the embodiments of the present disclosure to provide for a method and a device for an improved handling of a closing element in a laboratory automation system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
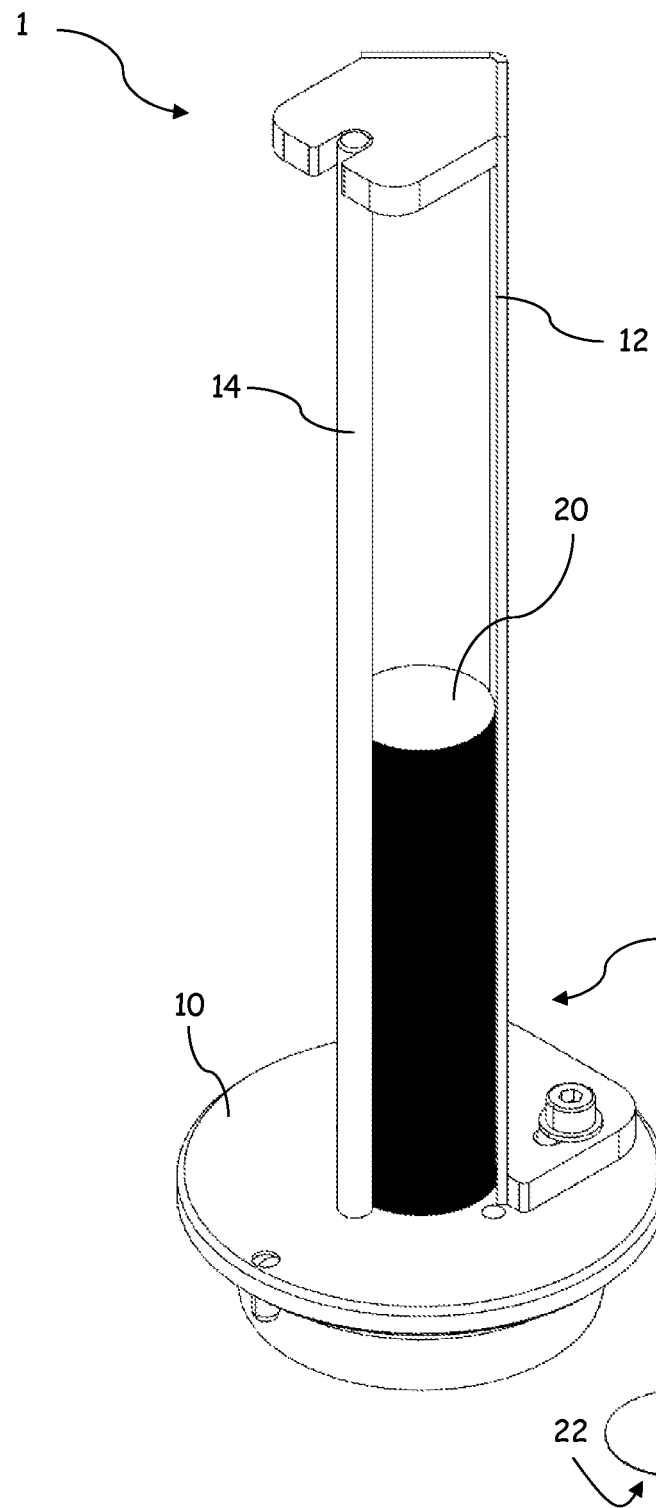
FIG. 1 illustrates a perspective view of a magazine storing a plurality of sealing foils and an isolated sealing foiling according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for handling a closing element in a laboratory automation system is provided. The closing element can be a sealing foil having at least two layers forming a first surface and an opposing second surface, respectively. The layers can differ in at least one material property. The method can comprise determining the material property on at least one of the first surface and the second surface for identifying the orientation of the sealing foil.

In one embodiment, one layer can be provided as a coating on the other layer or directly attached to the other layer. In other embodiments, the sealing foil can comprise the first and the second layer which can be connected by at least one third layer.

By the sealing foil, the test tubes may be sealed hermetically. However, for a proper sealing of the test tube by a sealing foil having different material properties on an upper and a lower surface or side, it can be mandatory to place the sealing foil with the correct orientation on the test tube. Depending on the device for bonding the sealing foil to the test tube, an incorrect orientation may also cause damage in the bonding or sealing device. The determining of the material property on at least one surface can allow for an automated identification of the orientation of the sealing foil.

In one embodiment, the material property can be determined quantitatively. In some embodiments, the material property can be determined qualitatively, wherein the outcome can be a binary signal. An orientation in one embodiment can be signaled optically and/or acoustically and/or, in the case of error detection, the laboratory automation system can be at least partly stopped and/or an error-recovery process can be triggered. The past-processing of such a binary signal for an optical and/or acoustical signaling and/or for triggering suitable error-recovery processes can be easy to implement.

In one embodiment, the sealing foil can be stored in a storage device with at least one of the first surface and the second surface being accessible. The material property can be determined on the accessible surface. A determination device may be incorporated in a pick-up device provided for a withdrawal of the sealing foil from the storage device. In some embodiments, the determination device can be incorporated in the storage device. In both embodiments, the orientation may be identified while the sealing foil is retained in the storage device and prior to its use. In one embodiment, the pick-up device, for example a gripper or a suction device, can be provided for transporting the sealing foil withdrawn from the storage device to a station comprising a bonding or sealing device for bonding the sealing foil to the test tube. In other embodiments, the pick-up device can be part of a sealing device. The pick-up device can be provided, for example, with a heating element for causing a sealing action. As the proper orientation may be verified prior or upon withdrawal of the sealing foil from the storage device, the pick-up device may be operated in case of an improper orientation in such manner, that the sealing foil having an improper orientation can be discarded.

In some embodiments, a plurality of sealing foils can be stacked in a magazine with one of the plurality of sealing foils being accessible for a withdrawal with the first surface or the second surface being presented. The material property can be determined on the presented surface, i.e. the first or second surface of the accessible sealing foil being presented. The sealing foils can be withdrawn from the magazine one by one. The material property of the presented surface of each sealing foil can be determined in order to avoid the processing of any improperly oriented sealing foil.

The material property to be determined can be selected by the person skilled in the art. Potential material properties to be determined at a surface are for example optical properties, such as, for example, reflectivity or color, thermal properties, such as, for example, thermal conductivity.

According to some embodiments, the closing element can be a sealing foil having an electrically non-conductive layer forming the first surface and an electrically conductive layer forming the second surface. The electrical conductivity on at least one of the first and the second surface can be determined for identifying the orientation of the sealing foil. In some embodiments, sealing foils comprising a metallic layer, such as, a layer of aluminum foil, and a second layer, which functions as adhesive layer or bonding layer can be used for sealing the test tubes. Heat can be applied to bond the sealing foil to the test tube. The metallic layer can have an electrical conductivity, whereas the adhesive layer or bonding layer can be electrically non-conductive or insulating. The material property to be measured can be the electrical conductivity.

In some embodiments, the electrical conductivity can be determined by a continuity test. For this purpose, two electrodes can be placed on the first surface and/or the second surface. By the continuity test, the electrical conductivity can be determined qualitatively and the outcome of the continuity test can be a binary signal. This binary signal may be processed suitably to avoid a use of the improperly oriented sealing foil.

The sealing foil may be stored or stacked in any orientation suitable for the handling in the subsequent sealing process. In some embodiments, the sealing foil can be arranged such that for a proper handling of the sealing foil, the electrically conductive layer can be presented. The electrical conductivity can be determined on the presented surface. In some embodiments, two electrodes can be placed on the presented surface for testing continuity. In the case the sealing foil is presented with an improper orientation, an interruption of the current flow can be detected.

A device for handling a closing element in a laboratory automation system is provided. The closing element can be a sealing foil having at least two layers forming a first surface and an opposing second surface, respectively. The layers can differ in at least one material property. The device can comprise a determination device for determining the material property on at least one of the first surface and the second surface for identifying the orientation of the sealing foil.

The determination device can allow for an automated detection of an improperly oriented sealing foil. The design of the determination device can depend on the material property to be determined and the determination method.

In some embodiments, the determination device can be arranged to qualitatively determine the material property. For example, the determination device can be arranged for identifying whether or not the surface analyzed is reflective, has a certain color, and the like.

In one embodiment, a storing device can be provided for storing the sealing foil with at least one of the first surface and the second surface being accessible. The determination device can be arranged for determining the material property of the accessible surface. The material property in one embodiment can be determined by a determination device, which can be fed to the storage device. In other embodiments, the determination device can be integrated into a pick-up device. In some embodiments, the determination device can be integrated in the storing device.

In some embodiments, the storing device can be a magazine, in which a plurality of sealing foils can be stacked with one of the plurality of sealing foils being accessible for a withdrawal with the first surface or the second surface being presented. The determination device can be arranged for determining the material property on the presented surface. The magazine for storing the sealing foils may have a design adapted to a pick-up device and/or the sealing foils.

The sealing foils can be stacked in the magazine in a vertical column with the lowest sealing foil being accessible for a withdrawal. The magazine can comprise at least two support surfaces for supporting the column of sealing foils. At least one of the support surfaces can be arranged as a measurement point of the determination device. The support surfaces in this case can be used for retaining the sealing foils against gravity in the magazine and as measuring points.

In some embodiments, the closing element can be a sealing foil having an electrically non-conductive layer forming the first surface and an electrically conductive layer forming the second surface. The determination device can be arranged for determining the electrical conductivity on at least one of the first surface and the second surface for identifying the orientation of the sealing foil.

The measurement device can comprise a continuity tester for determining the electrical conductivity by a continuity test. The continuity tester can comprise two electrodes to be placed in contact with the first surface or the second surface for determining whether or not the respective surface is electrically conductive. In the case the sealing foils are retained in a magazine stacked in a vertical column, two distinct support surfaces and/or two distinct areas of the magazine, which are electrically isolated, in one embodiment can be used as electrodes.

In some embodiments, for a proper handling of the sealing foil, the sealing foil can be arranged with the electrically conductive layer being presented. The determination device can be arranged for determining the electrical conductivity on the presented surface. In some embodiments, the determination device can be arranged for carrying out a continuity test at the presented surface. In case of a correct orientation, the presented surface can be electrically conductive and a current flow can be detected. In case of an improper orientation, the presented surface can be electrically non-conductive and a current flow can be inhibited.

In order to allow for a suitable reaction upon detection of an improperly oriented sealing foil, in one embodiment, the pick-up device can be arranged to discard such sealing foils. In alternative or in addition, in other embodiments, a signaling device can be provided for signaling an orientation of the sealing foil optically and/or acoustically and/or error recovery mode can be provided, which can be arranged to stop the laboratory automation system at least partly and/or to trigger an error-recovery process in case of an error detection.

A laboratory automation system can be provided comprising a number of pre-analytical, analytical and/or post-analytical stations for carrying out the method for handling a closing element in the laboratory automation system and/or with the device for handling a closing element in the laboratory automation system.

Figure 2:
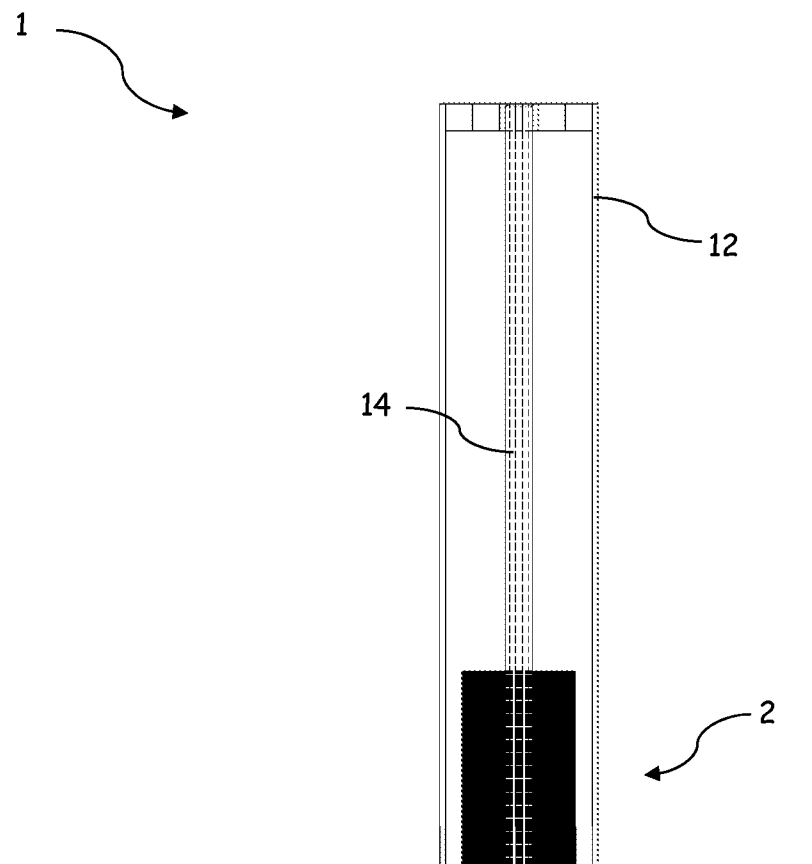
FIG. 2 illustrates a sectional view of the magazine of FIG. 1 according to an embodiment of the present disclosure.
Figure 2:
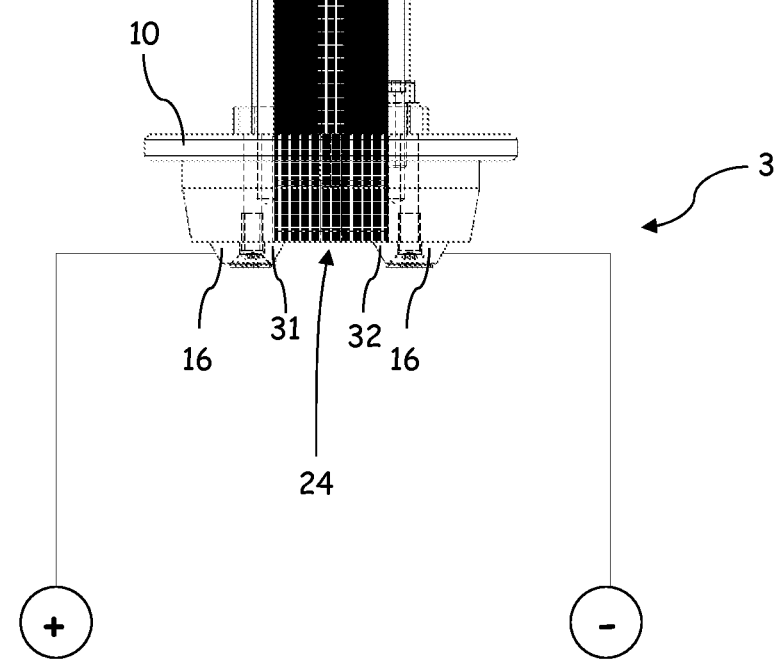

Referring initially to FIGS. 1 and 2, FIGS. 1 and 2 are a perspective view and a sectional view, respectively, of a magazine 1 storing a plurality of sealing foils 2. In addition, FIG. 1 illustrates an isolated sealing foiling 2. The sealing foils 2 can be used for recapping or reclosing a test tube in a laboratory automation system.

The magazine 1 shown in FIGS. 1 and 2 can comprise a base body 10 arranged for mounting the magazine to a station or a frame of the laboratory automation system. The magazine 1 can further comprise an angled wall element 12 and a retaining pin 14. A plurality of sealing foils 2 can be stacked in the magazine 1 in a vertical column. For inserting the sealing foils 2 in the magazine 1, the retaining pin 14 can be removed.

In one embodiment, the sealing foils 2 can have a circular shape. The base body 10 of the magazine 1 can have a through opening adapted to the shape of the sealing foils 2 allowing the sealing foils 2 to travel through the base body 10 and to be withdrawn from the magazine 1 at a bottom side of the base body 10. For retaining the sealing foils 2 in the magazine 1 against gravitational forces, at least two support surfaces 16 can be provided at the bottom side of the base body 10. In one embodiment, the support surfaces 16 can be screwed to the base body. Other fixation means can be possible.

The lowest sealing foil 2 can be withdrawn, for example, by a pick-up device designed as a suction device. The sealing foil 2 can be elastically deflected and released from the magazine 1.

The sealing foils 2 withdrawn from the magazine 1 can be used by a sealing device or capping device in order to seal a test tube. In one embodiment, the pick-up device can be provided for withdrawing the sealing foils 2 from the magazine and supplying the sealing foil 2 withdrawn to the sealing device or capping device. In other embodiments, the sealing device can be at least partly integrated in the pick-up device for withdrawing the sealing foils 2 from the magazine 1.

The sealing foils 2 can have at least two layers forming a visible first surface 20 and an opposing second surface 22. The sealing foils 2 may contain additional layers between the first surface 20 and the second surface 22. The layers forming the first surface 20 and the second surface 22 can differ in at least one material property. In one embodiment, the layer forming the first surface 20 can be an electrically non-conductive layer, whereas the layer forming the second surface 22 can be an electrically conductive layer.

Before being withdrawn from the magazine 1, the sealing foils 2 can be retained with one of the first surface 20 and the second surface 22 of the lowest sealing foil 2 being presented or uncovered. This presented or uncovered surface can be referred to as presented surface 24.

A proper sealing can only be possible in case the sealing foil 2, having a first surface 20 and a second surface 22 of different material properties, is placed on the test tube with a proper orientation.

A material property on at least one of the first surface 20 and the second surface 22 can be determined for identifying the orientation of the sealing foil 2. In one embodiment, an electrical conductivity of the presented surface 24 of the lowest sealing foil 2 can be determined by a continuity test.

For this purpose, in one embodiment, a determination device 3 comprising a first electrode 31 and a second electrode 32 can be provided, in which electrodes 31, 32 can contact the presented surface 24 of the lowest sealing foil 2.

Current can flow when the sealing foil 2 is arranged in a manner that the presented surface 24 is the second surface 22 provided with the electrically conductive layer. In case the sealing foil 2 is arranged in a manner that the presented surface 24 is the first surface 20 provided with the electrically non-conductive layer, a current flow can be inhibited. By evaluating the state of the respective electric circuit, an orientation of the lowest sealing foil 2 in the magazine can be identified. After the lowest sealing foil 2 has been withdrawn, the successive sealing foil can contact the electrodes 31, 32 and the orientation of this sealing foil 2 can be identified. Hence, the determination device 3 can allow for an identification of the orientation of each sealing foil 2 prior to its withdrawal.

In some embodiments, for a proper use of the sealing foils 2 for closing the test tubes, the sealing foils 2 can be arranged with the electrically non-conductive first surface 20 facing upwards, i.e. with the electrically conductive second surface being the presented surface 24.

In one embodiment, the determination device 3 can be integrated in the magazine 1. The support surfaces 16 can be used as the electrodes 31, 32, allowing for a compact arrangement. For this purpose, the base body 10 can be made from an electrically non-conductive material. In other embodiments, the determination device can be integrated in a pick-up device and/or can be designed as a separate device fed to the magazine 1 for determining the material property.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for handling a closing element in a laboratory automation system, wherein the closing element is a sealing foil having at least two layers forming a first surface and an opposing second surface, respectively, in which the at least two layers differ in at least one material property, the method comprising:
determining the material property on at least one of the first surface and the second surface for identifying the orientation of the sealing foil.

2. The method according to claim 1, wherein the material property is determined qualitatively.

3. The method according to claim 1, wherein a plurality of sealing foils is stacked in a magazine with one of the plurality of sealing foils being accessible for a withdrawal with the first surface or the second surface being presented, and wherein said material property is determined on the presented surface.

4. The method according to claim 1, wherein the closing element is a sealing foil having an electrically non-conductive layer forming the first surface and an electrically conductive layer forming the second surface and wherein the electrical conductivity on at least one of the first surface and the second surface is determined for identifying the orientation of the sealing foil.

5. The method according to claim 4, further comprising, determining the electrical conductivity on at least one of the first surface and the second surface for identifying the orientation of the sealing foil.

6. The method according to claim 5, wherein the electrical conductivity is determined by a continuity test.

7. The method according to 5, wherein for a proper handling of the sealing foil, the sealing foil is arranged such that the electrically conductive layer is presented and wherein the electrical conductivity is determined on the presented surface.

8. A device for handling a closing element in a laboratory automation system, wherein the closing element is a sealing foil having at least two layers forming a first surface and an opposing second surface respectively, in which the at least two layers differ in at least one material property, the device comprising:
 a determination device for determining the material property on at least one of the first surface and the second surface for identifying the orientation of the sealing foil.

9. The device according to claim 8, wherein the determination device is arranged to qualitatively determine the material property.

10. The device according to claim 8, further comprising, a magazine in which a plurality of sealing foils is stacked with one of the plurality of sealing foils being accessible for a withdrawal with the first surface or the second surface being presented.

11. The device according to claim 10, wherein the determination device is arranged for determining the material property on the presented surface.

12. The device according to claim 10, wherein the sealing foils are stacked in the magazine in a vertical column with the lowest sealing foil being accessible for a withdrawal.

13. The device according to claim 10, wherein the magazine comprises at least two support surfaces for supporting the column of sealing foils.

14. The device according to claim 13, wherein at least one of the support surfaces is arranged as a measurement point of the determination device.

15. The device according to claim 8, wherein the closing element is a sealing foil having an electrically non-conductive layer forming the first surface and an electrically conductive layer forming the second surface.

16. The device according to claim 15, wherein the determination device is arranged for determining the electrical conductivity on at least one of the first surface and the second surface for identifying the orientation of the sealing foil.

17. The device according to claim 16, wherein the measurement device comprises a continuity tester for determining the electrical conductivity by a continuity test.

18. The device according to claim 17, wherein the continuity tester comprises two electrodes for contacting one of the first surface or the second surface for determining the electrical conductivity of the surface.

19. The device according to claim 16, wherein for a proper handling of the sealing foil, the sealing foil is arranged with the electrically conductive layer being presented, and wherein the determination device is arranged for determining the electrical conductivity on the presented surface.

20. A laboratory automation system with a plurality of pre-analytical, analytical and/or post-analytical stations for carrying out a method according to claim 1 and/or with a device according to claim 8.

* * * * *